United States Patent [19]

Raduechel et al.

[11] Patent Number: 4,806,668
[45] Date of Patent: Feb. 21, 1989

[54] PROCESS FOR THE PRODUCTION OF 9BETA-CHLOROPROSTAGLANDINS

[75] Inventors: Bernd Raduechel; Werner Skuballa; Helmut Vorbrueggen, all of Berlin, Fed. Rep. of Germany

[73] Assignee: Schering Aktiengesellschaft, Berlin and Bergkamen, Fed. Rep. of Germany

[21] Appl. No.: 110,745

[22] PCT Filed: Nov. 28, 1986

[86] PCT No.: PCT/DE86/00483
§ 371 Date: Aug. 7, 1987
§ 102(e) Date: Aug. 7, 1987

[87] PCT Pub. No.: WO87/03582
PCT Pub. Date: Jun. 18, 1987

[30] Foreign Application Priority Data
Dec. 10, 1985 [DE] Fed. Rep. of Germany ....... 3543991

[51] Int. Cl.$^4$ .............................. C07F 7/08; C07F 7/18
[52] U.S. Cl. ....................................... 556/436; 568/426
[58] Field of Search .......................... 556/436; 568/426

[56] References Cited

U.S. PATENT DOCUMENTS 4,039,563 8/1977 Tanaka et al. .................. 556/436 X
4,703,127 10/1987 Rickards et al. ................ 556/436 X

FOREIGN PATENT DOCUMENTS 0053979 6/1982 European Pat. Off. ........ 556/436 X

Primary Examiner—Paul F. Shaver
Attorney, Agent, or Firm—Millen & White

[57] ABSTRACT

The invention relates to a process for the production of (5-chloro-3-hydroxycyclopentyl) acetaldehydes of formula II

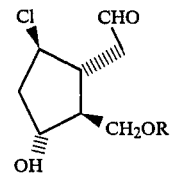

in which R signifies a benzyl radical, a tert-butyldimethylsilyl radical or a tert-butyldiphenylsilyl radical, characterized in that a compound of formula I

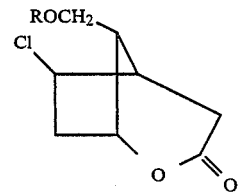

in which R has the meanings already mentioned, is reduced in the presence of a reduction agent.

2 Claims, No Drawings

PROCESS FOR THE PRODUCTION OF 9BETA-CHLOROPROSTAGLANDINS

This invention relates to a process for the production of 9beta-chloroprostaglandins, 9beta-Chloroprostaglandins are described in the following publications:
1. Chem., Biochem., Pharmacol. Act. Prostanoids, Incl. Proc. Symp. 1978 (Pub. 1979) 39–60, see also Chemical Abstracts 91, 107690 f
2. Prostaglandins 16, 47–65 (1978), see also Chemical Abstracts 89, 146467 s
3. J. Am. Chem. Soc. 99, 7738 (1977)
4. Advances in Prostaglandin, Thromboxane and Leukotriene Research 14, 274 (1985)
5. European Patent Specification No. 0 030 377.

Generally 9-chloroprostaglandins are produced from the corresponding 9-hydroxy compounds or the corresponding 9-sulfonic acid esters by reaction with a chlorocompound. In this case, mixtures always occur of the desired 9-chloroprostaglandin derivative and the $\Delta^{8,9}$ or $\Delta^{9,10}$ olefins, which so far in some cases could be separated only with great expense.

These experimental difficulties can be circumvented by starting with a crystal-clear product which already contains chlorine and which starting from easily available initial materials can be produced without difficulties.

9-Chloroprostaglandins are valuable drugs (see loc. cit. 1 and 5). With Nocloprost (1) in the case of test subjects stomach mucous membrane damages, as they are caused by nonsteroid anti-inflammatory agents, can be prevented or at least greatly diminished.

The invention serves for the simplified production of important active substances. The process according to the invention is to be explained more in detail by the production of Nocloprost. For a man of the art it is possible on the basis of this invention to produce an abundance of other 9-chloroprostaglandins.

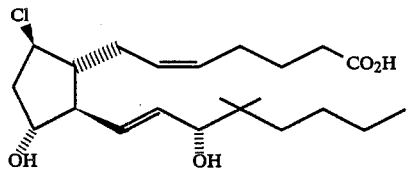

1

The invention includes the production of the intermediate product of formula II for the production of 9-chloroprostaglandins.

Thus, the invention relates to a process for the production of (5-chloro-3-hydroxycyclopenyl)acetaldehydes of formula II

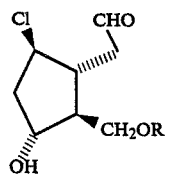

II in which R signifies a benzyl radical, a tertbutyldimethylsilyl radical or a tert-butyldiphenylsilyl radical, characterized in that a compound of formula I

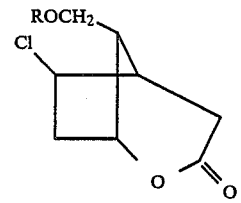

I in which R has the meanings already mentioned, is reduced in the presence of a reduction agent, preferably diisobutylaluminum hydride.

The reduction is performed in hydrocarbons, preferably toluene, at temperatures between −120° C. and −20° C., preferably at −70° C.

For conversion of the compounds of formula II into 9beta-chloroprostaglandins the hydroxy group in II is protected by reaction with dihydropyran as tetrahydropyranyl ether III. This is followed by a cleavage of protection group R to IV. For the case of R=benzyl, the cleavage is performed under hydrogenolytic conditions with hydrogen in the presence of palladium catalysts. For the case of R=tert-butyldimethylsilyl or tert-butyldiphenylsilyl the cleavage is performed with tetrabutylammonium fluoride, with the operation preferably being performed at −20° C. to avoid the elimination of hydrogen chloride.

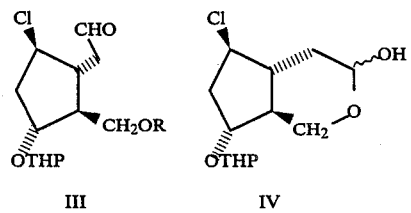

III    IV

The compound IV is reacted with the ylene from 4-carboxybutyltriphenylphosphonium bromide to compound V, from which methyl ester VI is obtained with diazomethane. Then oxidation is performed with Collins reagent or according to the Swern method to aldehyde VII, which by reaction with the anion from 3,3-dimethyl-2-oxoheptane phosphonic acid dimethyl ester is converted into unsaturated ketone VIII. But at this point any other substituted or unsubstituted 2-oxo-alkyl or 2-oxo-aralkyl phosphonic acid ester can be used, so that an abundance of 9beta-chloroprostaglandins with modified lower side chain becomes available.

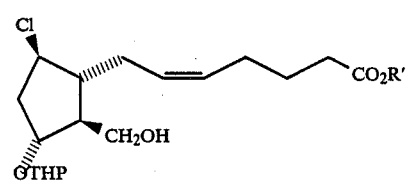

V  R' = H
VI R' = CH₃

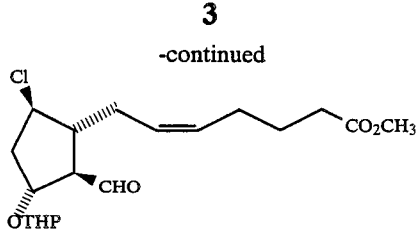

VII

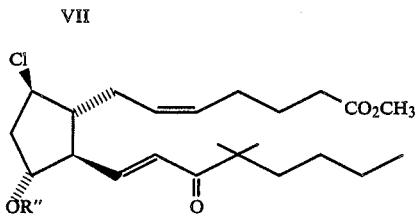

VIII R″ = THP
IX  R″ = H

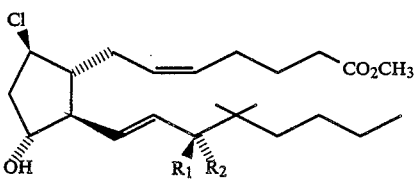

X  R₁ = H, R₂ = OH
XI R₁ = OH, R₂ = H

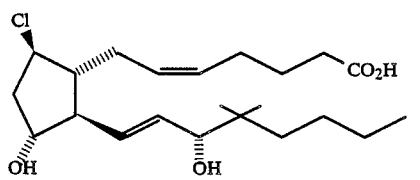

1

EXAMPLE 1

(±)-(1R,2S,3R,5R)-(benzyloxymethyl-5-chloro-3-hydroxycyclopentyl)acetaldehyde (II, R=CH₂C₆H₅)

1 g of (±)-8-anti-benzyloxymethyl-6-oxo-chloro-3-oxo-2-oxabicyclo[3.2.1]octane (I, R=CH₂C₆H₅) is dissolved in 20 ml of toluene and mixed drop by drop at −78° C. with 5.9 ml of a 1.2M solution of diisobutylaluminum hydride in toluene. It is stirred for 30 minutes more at −78° C., then mixed with 05. ml of isopropyl alcohol and 3 ml of water, stirred for 1 hour at 20° C., filtered and the solution concentrated by evaporation. 0.97 g of II (R=CH₂C₆H₅) as colorless oil. IR: 3600, 3410 (br.), 2998, 2862, 2835, 1725, 1451, 1362, 1095/cm

EXAMPLE 2

(a)

(+)-(1R,2S,3R,5R)-[2-benzyloxymethyl-5-chloro-3-(tetrahydropyran-2-yloxy)-cyclopentyl]-acetaldehyde(III) (R=CH₂C₆H₅)

12 g of II(R=CH₂C₆H₅) is dissolved in 250 ml of dichloromethane and mixed with 5.2 g of dihydropyran and 40 mg of p-TsOH at 0° C. It is stirred for 30 minutes at 0° C., diluted with 200 ml of dichloromethane, shaken in succession with sodium bicarbonate solution and salt water, dried over magnesium sulfate and concentrated by evaporation in a vacuum. 14.5 g of III (R=CH₂C₆H₅). IR: 2950, 2878, 2740, 1728, 1121/cm.

(b)

(±)-(1R,2S,3R,5R)-[5-chloro-2-hydroxymethyl-3-tetrahydropyran-2-yloxy)-cyclopentyl]-acetaldehyde hemiacetal (IV)

A solution of 9.5 g of III (R=CH₂C₆H₅) in 200 ml of ethyl acetate is shaken with 950 mg of palladium (10% on carbon) under hydrogen until absorption of 1 equivalent of hydrogen. Filtration, concentration by evaporation in a vacuum are performed and the residue is recrystallized from diethyl ether/hexane (1:1) and 5.9 g of IV, mp: 78°–80° C. is obtained.

IR: 3600, 3410 (br.), 3000, 2942, 2870, 2851, 1723 (weak), 1439, 1117, 1072, 1027, 988/cm.

(c)

(±)-(Z)-7-[(1R,2S,3R,5R)-5-chloro-2-hydroxymethyl-3-(tetrahydropyran-2-yloxy)-cyclopentyl]-5-heptenic acid methyl ester (VI)

47.5 ml of a 1.6M solution of butyllithium in hexane is instilled into a solution of 16.4 ml of hexamethyldisilazane in 50 ml of tetrahydrofuran at 0° C. After 15 minutes this solution is instilled into 160 ml of tetrahydrofuran at 0° C. to a stirred suspension of 17.3 g of 4-carboxybutyltriphenylphosphonium bromide. It is stirred for 1 more hour at 0° C., then cooled to −78° C. and a solution of 1.80 g of IV in 20 ml of tetrahydrofuran is instilled within 20 minutes. Then it is stirred 1 hour at −40° C. and for another hour at 0°, then poured onto water, acidified with citric acid to pH 4 and extracted with ether. This solution of carboxylic acid V is mixed at 0° C. with ethereal diazomethane solution to permanent yellowing. It is concentrated by evaporation in a vacuum and the residue is purified by chromatography on silica gel with hexane/10–40% diethyl ether and 1.45 g of VI is obtained as colorless oil.

IR: 3430 (br.), 2998, 2948, 2870, 1729, 1437, 1130, 1028/cm.

(d)

(±)-(5Z)-7-[(1R,2R,3R,5R)-5-chloro-2-formyl-3-(tetrahydropyran-2-yloxy)-cyclopentyl]-5-heptenic acid methyl ester (VII)

9 g of Collins reagent is dissolved in 85 ml of dichloromethane, and a solution of 2 g of VI in 25 ml of dichloromethane is instilled with stirring in 5 minutes, stirred 15 minutes, diluted with 200 ml of diethyl ether, shaken with sodium bicarbonate solution, diluted sulfuric acid and salt water, dried over magnesium sulfate and concentrated by evaporation in a vacuum. 1.72 g of aldehyde VII is obtained as oil.

IR: 2998, 2951, 2872, 2838, 1730, 1439, 1130, 1031/cm.

(e)

(±)-(5Z)-7-{(1R,2R,3R,5R)-5-chloro-2-[(E)-4,4-dimethyl-3-oxo-1-octenyl]-3-(tetrahydropyran-2-yloxy)-cyclopentyl}-5-heptenic acid methyl ester (VIII)

294 mg of 55% sodium hydride is suspended in 25 ml of dimethoxyethane, and 1.53 g of 3,3-dimethyl-2-oxoheptanephosphonic acid dimethyl ester is instilled. It is stirred for another 30 minutes, cooled to −20° C., and a solution of 1.98 g of VII in instilled in 10 ml of dimethoxyethane and 10 ml of tetrahydrofuran. After 1 hour it is allowed to warm to room temperature, mixed with 0.5 ml of glacial acetic acid, diluted with 200 ml of diethyl ether, shaken three times with 20 ml of salt water each, dried over magnesium sulfate and evaporated in a vacuum to dryness. The residue is chromatographed on silica gel with hexane/5–25% diethyl ether. 1.62 g of VIII is obtained as colorless oil. IR: 2998, 2955, 2863, 1730, 1684, 1621, 1437, 1060, 978/cm.

(f)

(±)-(Z)-7-{(1R,2R,3R,5R)-5-chloro-2-[(E)-4,4-dimethyl-3-oxo-1-octenyl]-3-hydroxy-cyclopentyl}-5-heptenic acid methyl ester heptenic acid methyl ester (IX)

1 g of VIII is stirred for 24 hours at 40° C. with 25 ml of a mixture of glacial acetic acid-water-tetrahydrofuran (65/35/10). It is concentrated by evaporation in a vacuum, chromatographed on silica gel with hexane/1-0–50% ethyl acetate, and 720 mg of IX is obtained as oil.

IR: 3600, 3410 (br.), 2998, 2951, 2855, 1730, 1685, 1620, 1055, 978/cm.

(g)

(±)-(Z)-7-{(1R,2R,3R,5R)-5-chloro-3-hydroxy-2-[(E)-(3R)-3-hydroxy-4,4-dimethyl-1-octenyl]-cyclopentyl}-5-heptenic acid methyl ester (X)

A solution of 600 mg of IX in 25 ml of methanol is mixed with 60 mg of cerium(III) chloride with stirring and then 500 mg of sodium borohydride is added at −40° C. After 1 hour, thin-film chromatography checking shows a complete reduction. It is installed with 1 ml of glacial acetic acid, concentrated by evaporation in a vacuum, diluted with water and extracted several times with dichloromethane. The combined organic phases are washed with sodium bicarbonate solution and salt water, dried over magnesium sulfate and concentrated by evaporation in a vacuum. The residue is chromatographed on silica gel with dichloromethane/1–10% acetane. First 280 mg of XI is eluted as nonpolar component and then 295 mg of the desired epimer X, both as colorless oils.

IR: (for X): 3603, 3425, (br.), 2999, 2959, 2932, 2873, 1730, 1437, 974/cm.

(h)

(±)-(Z)-7-{(1R,2R,3R,5R)-5-chloro-3-hydroxy-2-[(E)-(3R)-3-hydroxy-4,4-dimethyl-1-octenyl]-cyclopentyl}-5-heptenic acid (1, Nocloprost)

440 mg of X is dissolved in 10 ml of a mixture, which consists of 5 g of potassium hydroxide, 187 ml of ethanol and 62 ml of water, allowed to stand 4 hours at 25° C., concentrated by evaporation in a vacuum and diluted with 50 ml of water. The aqueous solution is extracted with 50 ml of ether/hexane (1:1) and this extract discarded. The aqueous phase is acidified with citric acid to pH 5, extracted several times with dichloromethane, the combined extracts washed with salt water, dried over magnesium sulfate and concentrated by evaporation in a vacuum. Thus 400 mg of 1 is obtained as colorless oil.

IR: 3600, 3405 (br.), 2999, 2961, 2938, 2875, 1712, 974/cm.

EXAMPLE 3

(a)

(±)-(Z)-7-[(1R,2S,3R,5R)-2-benzyloxymethyl-5-chloro-3-(tetrahydropyran-2-yloxy)-cyclopentyl]-5-heptenic acid methyl ester (XIII, R=CH$_2$C$_6$H$_5$)

36.7 ml of hexamethyldisilazane is dissolved in 60 ml of tetrahydrofuran and 82 ml of 1.55M of butyllithium solution in hexane is instilled. It is stirred two 2 hours more at 0° C. and this solution is instilled also at 0° C. into a stirred suspension of 30 g of 4-carboxybutyl-triphenyl-phosphonium bromide in 150 ml of tetrahydrofuran. After 1 hour it is cooled to −78° C. and a solution of 10.5 g of III (R=CH$_2$C$_6$H$_5$) in 50 ml of tetrahydrofuran is instilled within 15 minutes. Then, in the course of 2 hours it is allowed to come to room temperature, stirred two more hours and then diluted with water, adjusted to pH 4 with citric acid, extracted with dichloromethane, the extract is washed with salt water, dried over magnesium sulfate, concentrated by evaporation in a vacuum, and carboxylic acid XII (R=CH$_2$C$_6$H$_5$) is obtained.

For conversion to methyl ester, the residue is dissolved in 150 ml of diethyl ether and mixed at 0° C. with ethereal diazomethane solution to permanent yellowing, it is concentrated by evaporation in a vacuum and the residue is chromatographed on silica gel with hexane/10–60% ethyl acetate. 7.05 g of XIII (R=CH$_2$C$_6$H$_5$) is obtained as colorless oil.

IR: 2998, 2943, 2855, 1731, 1452, 1438, 1075, 1028/cm.

(b)

(±)-(Z)-7-[(1R,2S,3R,5R)-5-chloro-2-hydroxymethyl-3-(tetrahydropyran-2-yloxy)-cyclopentyl]heptanic acid methyl ester (XIV)

6.50 g of XIII (R=CH$_2$C$_6$H$_5$) is shaken in 150 ml of ethyl acetate and 1 ml of glacial acetic acid with 1.30 g of palladium on carbon (10%) under a hydrogen atmosphere to absorption of 2 equivalents of H$_2$, filtered, shaken with 20% potassium bicarbonate solution and salt water, dried over magnesium sulfate and concentrated by evaporation in a vacuum. For purification it is chromatographed on silica gel with hexane/10–50% diethyl ether, and 4.50 g of XIV is obtained as colorless oil.

IR: 3450 (br.), 2930, 2860, 1732, 1438, 1132, 1075, 1028/cm.

(c)

(±)-(Z)-7-[(1R,2R,3R,5R)-5-chloro-2-formyl-3(tetrahydropyran-2-yloxy)-cyclopentyl]heptanic acid methyl ester (XVII)

10 ml of pyridine is instilled into a suspension of 8.25 g of chromium(VI) oxide in 210 ml of dichloromethane with intensive stirring, it is stirred for 20 more minutes at room temperature and then again cooled to 0° C. A solution of 3.89 g of XIV in 60 ml of dichloromethane is quickly instilled in this reagent. It is stirred for another 15 minutes, then diluted with ice cold diethyl ether and shaken, in succession, with saturated potassium bicarbonate solution, 10% sulfuric acid and salt water, dried over magnesium sulfate and concentrated by evaporation in a vacuum. 3.68 g of XVII is obtained as brown oil. IR: 2935, 2860, 2720, 1725, 1438, 1125, 1075, 1028/cm.

(d)

(±)-(Z)-7-[(1R,2R,3R,5R)-5-chloro-2-[(E)-4,4-dimethyl-3-oxo-1-octenyl]-3-(tetrahydropyran-2-yloxy)-cyclopentyl]heptenic acid methyl ester (XVIII)

2.82 g of 3,3-dimethyl-2-oxo-heptanephosphonic acid dimethyl ester dissolved in 40 ml of dimethoxyethane is instilled at 0 C. in a suspension of 542 mg of sodium hydride in 40 ml of dimethoxyethane. It is stirred for 30 minutes at room temperature, then cooled to $-15°$ C. and 3.65 g of XVII dissolved in 45 ml of dimethoxyethane is instilled within 10 minutes. Then, it was stirred 1 hour at 0° C. and 1 hour at room temperature. For working up, it was mixed at 0° C. with 1 ml of glacial acetic acid and 500 ml of water, then extracted several times with diethyl ether, and the combined extracts, in succession, shaken with sodium bicarbonate solution and salt water, dried over magnesium sulfate and concentrated by evaporation in a vacuum. The residue was chromatographed on silica gel with hexane/10–40% diethyl ether. 3.68 g of XVIII was obtained as colorless oil.

IR: 2932, 2859, 1731, 1686, 1621, 1465, 1438, 1075, 1028, 980/cm.

(e)

(±)-7-[(1R,2R,3R,5R)-5-chloro-2-[(E)-(3R)-3-hydroxy-4,4-dimethyl-1-octenyl]-3-(tetrahydropyran-2-yloxy)-cyclopentyl]heptanic acid methyl ester (XIX)

To a solution of 1 g of XVIII in 50 ml of methanol are added at $-20°$ C. 1 g of sodium borohydride and after 30 minutes again 1 g of sodium hydride. After another 30 minutes the reaction solution is slowly poured onto a pH 4 citrate buffer, then shaken out several times with dichloromethane, dried over magnesium sulfate and concentrated by evaporation in a vacuum. The residue consists of a mixture of the two epimeric alcohols XIX and XX.

For separation, it is chromatographed on silica gel with hexane/10–50% diethyl ether, and 450 mg of XX is obtained as nonpolar component and 510 mg of XIX at polar component, both as coloress oils.

IR: (for XIX): 3600, 3460 (br.), 2930, 2861, 1730, 1438, 1075, 1028, 975/cm.

(f)

(±)-(Z)-7-{(1R,2R,3R,5R)-5-chloro-3-hydroxy-2-[(E)-(3R)-3-hydroxy-4,4-dimethyl-1-octenyl]-cyclopentyl}-heptanic acid methyl ester (XXI)

1.02 g of XIX is stirred 48 hours with 10 ml of a mixture of glacial acetic acid-water-tetrahydrofuran (65/35/10), concentrated by evaporation in a vacuum, diluted with 150 ml of dichloromethane, shaken, in succession, with potassium bicarbonate solution and salt water, dried over magnesium sulfate and concentrated by evaporation in a vacuum. The residue is chromatographed on silica gel with hexane/10–50% diethyl ether, and 710 mg of XXI is obtained as colorless oil.

IR: 3600, 3410 (br.), 2952, 2860, 1731, 1438, 974/cm.

(g)

(±)-(Z)-7-{(1R,2R,3R,5R)-5-chloro-3-hydroxy-2-[(E)-(3R)-3-hydroxy-4,4-dimethyl-1-octenyl]-cyclopentyl} heptanic acid (2, 5,6-dihydronocloprost)

To a solution of 600 mg of XXI in 8 ml of ethanol is added 8 ml of 0.7N potassium hydroxy solution. After 3 hours it is concentrated by evaporation in a vacuum, diluted with 80 ml of water and extracted with 50 ml of diethyl ether. This extract is discarded. The aqueous phase is adjusted with citric acid to pH 4 and extracted several times with dichloromethane. The combined extracts are dried and concentrated by evaporation in a vacuum. 540 g of 2 is obtained as colorless oil.

IR: 3600, 3420 (br.), 2953, 2860, 1712, 1465, 1075, 974/cm.

EXAMPLE 4

(a)

(±)-5-exo-chloro-2,2-ethylenedioxy-bicyclo-[2,2,1]-heptane-7-anti-carboxylic acid (XXIII)

(a) 36.5 g of (±)-5-exo-chloro-2-oxobicyclo[2,2,1]heptane-7-anti-carboxylic acid (XXIII) is refluxed for 3 hours in 500 ml of benzene with 13 ml of ethylene glycol and 365 mg of p-toluenesulfonic acid, and the resulting water is separated by a separator. Cooling to 5° C. is performed, the precipitated crystals are suctioned off, rewashed with toluene/hexane (2:1) and the crystal paste is dried in a vacuum. 39.4 g of XXIII is obtained, mp: 168°–169° C.

IR: 3420, 2995, 2895, 1715, 1330, 1158, 1112, 1078, 1022, 958, 905/cm.

(b)

(±)-5-exo-chloro-2,2-ethylenedioxy-bicyclo[2,2,1]heptane-7-anti-carboxylic acid methyl ester (XXIV)

6.98 g of XXIII is dissolved in 50 ml of dimethylformamide, mixed with 3.1 ml of methyl iodide and 4.14 g of potassium carbonate and stirred 24 hours at room temperature. It is then diluted with 500 ml of ice water and shaken out twice with 200 ml of pentane/diethyl ether (1:1) each, the organic phase is washed with 50 ml of salt water, dried over magnesium sulfate and concentrated by evaporation in a vacuum. The residue is recrystallized from hexane/diethyl ether. 5.35 g of XXIV is obtained. Mp: 71°–72° C.

IR: 2962, 2902, 1737, 1440, 1332, 1159, 1110, 1078, 1038, 1023, 960, 915, 903/cm.

(c)

(±)-5-exo-chloro-2,2-ethylenedioxy-7-anti-hydroxymethylbicyclo[2,2,1]heptane (XXV)

39.5 g of XXIV dissolved in 1 liter of ether is instilled with stirring in a suspension of 9.11 g of lithium alanate in 1 liter of diethyl ether within 30 minutes. Then it is refluxed for 2 hours, cooled to 0° C. and 100 ml of ethyl acetate is slowly instilled, stirred for 1 hour, diluted with 0.5 liter of diethyl ether and 20 ml of water is carefully instilled. After 30 minutes, it is filtered, dried over magnesium sulfate and concentrated by evaporation in a vacuum. 33.0 g of XXV is obtained at colorless oil.

IR: 3600, 3470 (br.), 2980, 1330, 1115, 1072, 1023, 980, 951, 907, 845/cm.

(d)

(±)-7-anti-benzyloxymethyl-5-exo-chloro-2,2-ethylenedioxy-bicyclo[2,2,1]heptane (XXVI)

12 g of sodium hydride (55%) is stirred with 100 ml of hexane, then the hexane is decanted and the residue mixed with 400 ml of dimethylformamide. 48.7 g of XXV dissolved in 40 ml of dimethylformamide is instilled into this suspension with stirring. It is stirred for 1 hour and then 41.9 g of benzyl bromide is instilled and stirred for 24 hours. It is carefully mixed with 1.5 liters of water and extracted several times with pentane. The combined extracts were washed with salt water, dried over magnesium sulfate and concentrated by evaporation in a vacuum. The residue is distilled at 0.1 torr in a bulb tube at a bath temperature of 100° C. 45.7 g of XXVI is obtained as colorless liquid.

IR: 2976, 2878, 1451, 1327, 1098/cm.

(e)

(±)-7-anti-benzyloxymethyl-5-exo-chloro-2-oxo-bicyclo[2,2,1]heptane (XXVII)

A solution of 55 g of XXVI in 1.10 liter of acetone is mixed with 220 ml of 10% by volume of sulfuric acid and refluxed for 3 hours. It is concentrated by evaporation in a vaccum, diluted with 500 ml of water, extracted several times with dichloromethane, the extract is washed with salt water, dried over magnesium sulfate and concentrated by evaporation in a vacuum. The liquid residue is distilled at 0.1 torr and 90° C. bath temperature in a bulb tube. 43 g of XXVII is obtained as colorless liquid.

IR: 3005, 2920, 2861, 1749, 1452, 1098/cm.

(f)

(±)-8-anti-benzyloxymethyl-6-exo-chloro-3-oxo-oxabicyclo[3,2,1]octane (I,R=CH$_2$C$_6$H$_5$)

A solution of 20 g of XXVII in 400 ml of dichloromethane is stirred at 0° C. for 3 hours with 10.8 g sodium bicarbonate and 29.3 g of m-chloroperbenzoic acid (85%). It was then mixed with 400 ml of 5% sodium hydrogen sulfite solution, shaken, the aqueous phase is extracted with dichloromethane, the organic phases are combined, washed with sodium bicarbonate solution and salt water, dried and concentrated by evaporation in a vacuum. The residue is chromatographed on silica gel with hexane/ethyl acetate (7:3) and the clean fractions recrystallized from diethyl ether/hexane (1:1). 11.9 g of I (R=CH$_2$C$_6$H$_5$) is obtained, mp: 74°–75° C. IR: 3030, 2998, 2861, 1738, 1452, 1363, 1164, 1119, 1032/cm.

EXAMPLE 5

(±)-5-exo-chloro-2-oxobicyclo[2,2,1]heptane-7-anti-carboxylic acid (+)-(XXII)

(a) A solution of 15 g of 2-oxotricyclo[2,2,,1,0$^{3,5}$]heptane-7-anticarboxylic acid in 600 ml of acetone is mixed at 0° C. with 11.47 g of triethylamine and 15.49 g of chloroformic acid isobutyl ester. After 30 minutes 16.91 g of D-(−)-2-amino-2-phenylethanol dissolved in a mixture of 138 ml of acetone and 138 ml of acetonitrile is instilled. After 2 hours stirring at room temperature it is concentrated by evaporation in a vacuum, diluted with 1.5 liters of dichloromethane and washed three times with 100 ml of salt water each, dried over magnesium sulfate and concentrated by evaporation in a vacuum. The residue is chromatographed on silica gel with hexane/ethyl acetate (20–80%). 6.10 g of the nonpolar amide 2-oxotricyclo[2.2.1.0$^{3,5}$]heptane-7-anti-D-(−)-2-amino-2-phenylethanol]-carboxamide (XXXI) and 5.95 g of polar amide (XXXI (both viscous oils) besides 4 g of a mixture of the two amides are obtained. In a thin-film chromatogram the separated amides exhibit homogeneous spots on the silica gel plates (mobile solvent: ethyl acetate/hexane 9:1) with Rf value of 0.31 or 0.24.

The IR spectrum of the two amides are almost identical, while differences can be seen in the NMR spectrum.

IR: (pol. amide): 3600, 3435, 3030, 2958, 2890, 1760, 1669, 1508, 950, 841, 702/cm (b) 3.68 g of nonpolar amide XXXI is refluxed with 40 ml of concentrated hydrochloric acid for 5 hours. It is then diluted with 100 ml of water, extracted three times with 50 ml of ethyl acetate, the combinded extracts washed with 20 ml of salt water, dried over magnesium sulfate and concentrated by evaporation in a vacuum. The residue is recrystallized from ethyl acetate/hexane and 2.10 g of (+)-XXII is obtained, mp: 151°–152° C., [alpha$_D$]+13.6° (C=1 in methanol).

IR: 3510, 3005, 2960, 1761, 1712, 1292, 949, 840/cm.

EXAMPLE 6

If the same reaction steps are performed with the polar amide XXXI, then (−)-XXII is obtained, mp: 156°–157° C., [alpha$_D$]−13.0° (C=1 in methanol).

EXAMPLE 7

If the carboxylic acid (+)-XXII, produced according to example 6, is used as a start and it is reacted according to example 2 (for synthesis of 1), then Nocloprost is obtained in optically active physiologically effective levorotatory form, [alpha]$_D$ −10.2° (C=0.5 in dioxane).

We claim:

1. Process for the production of (5-chloro-3-hydroxycyclopentyl)acetaldehydes of formula II

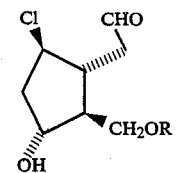

in which R signifies a benzyl radical, a tert-butyldimethylsilyl radical or a tert-butyldiphenylsilyl radical, characterized in that a compound of formula I

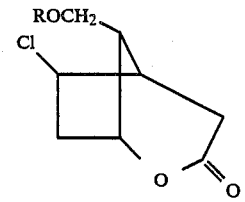

in which R has the meanings already mentioned, is reduced in the presence of a reduction agent.

2. Process according to claim 1, wherein diisobutylaluminum hydride is used as reducing agent.

* * * * *